United States Patent [19]

Kórösi et al.

[11] 4,423,044
[45] Dec. 27, 1983

[54] 3,4-DIHYDRO-5H-2,3-BENZODIAZEPINE DERIVATIVES AND PHARMACEUTICAL USE THEREOF

[75] Inventors: Jenő Kórösi; Tibor Láng; Ferene Andrási; József Székely; Tamás Hámori; Tibor Balogh; Lajos Ila; Katalin Goldschmidt; Eleónora Sinèger; Imre Moravcsik, all of Budapest, Hungary

[73] Assignee: Egyt Gyógyszervegyészeti Gyár, Budapest, Hungary

[21] Appl. No.: 352,346

[22] Filed: Feb. 25, 1982

[30] Foreign Application Priority Data

Mar. 12, 1981 [HU] Hungary .................. 620/81

[51] Int. Cl.³ .................... A61K 31/55; C07D 243/00; C07D 405/04; C07D 409/04
[52] U.S. Cl. ..................... 424/244; 260/239 BD; 260/330.3; 260/330.9; 424/275; 424/285
[58] Field of Search .......... 260/239 BD, 330.3, 330.9; 424/244, 275, 285

[56] References Cited

U.S. PATENT DOCUMENTS

| Re. 30,014 | 5/1979 | Korosi et al. | 260/239 |
| 3,736,315 | 5/1973 | Korosi et al. | 260/239 |
| 4,322,346 | 3/1982 | Korosi et al. | 260/239 |

OTHER PUBLICATIONS

Schmitz et al., Ber. Dent. Chem., vol. 95, pp. 2012–2017 (1962).
Lempert-Shréter, Acta. Chim. Acad. Scien. Hung., vol. 83, pp. 115–117 (1974).
Van Der Stelt et al., Rec. Tran. Chim., vol. 84, pp. 633–645 (1965).

*Primary Examiner*—Alton D. Rollins
*Attorney, Agent, or Firm*—Keil & Witherspoon

[57] ABSTRACT

The invention relates to new 3,4-dihydro-5H-2,3-benzodiazepine derivatives of general formula (I) and pharmaceutically acceptable acid addition salts thereof,

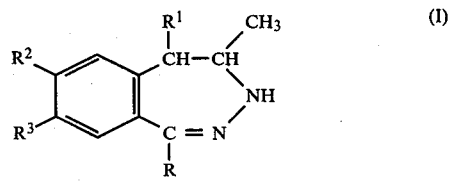

wherein
R represents a phenyl group optionally carrying one or two substituents selected from the group consisting of halogen, hydroxy, $C_{1-4}$ alkoxy and benzyloxy; a furyl or a thienyl group,
$R^1$ stands for a hydrogen atom or a $C_{1-4}$ alkyl group,
$R^2$ and $R^3$ each represent hydrogen atom, $C_{1-4}$ alkoxy, $C_{4-7}$ cycloalkoxy or benzyloxy group.

The new compounds of the general formula (I) can be prepared by reducing a 5H-2,3-benzodiazepine derivative of the general formula (II)

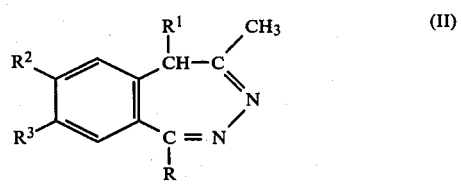

wherein R, $R^1$, $R^2$ and $R^3$ have the above-defined meanings, with an inorganic or organic hydride and/or complex metal hydride.

The new compounds of the general formula (I) possess significant central nervous effects and can advantageously be used in the therapy.

9 Claims, No Drawings

3,4-DIHYDRO-5H-2,3-BENZODIAZEPINE DERIVATIVES AND PHARMACEUTICAL USE THEREOF

The invention relates to new 3,4-dihydro-5H-2,3-benzodiazepine derivatives, a process for the preparation thereof, furthermore to pharmaceutical compositions containing the same.

It is known that the 1-(3,4-dimethoxyphenyl)-3-acetyl-4-methyl-5-ethyl-7,8-dimethoxy-3,4-dihydro-5H-2,3-benzodiazepine can be prepared by the catalytic hydrogenation of the corresponding 4-methylidene derivative [Acta Chim. (Budapest) 83, 115 (1974)]. Three further compounds have also been produced by reacting the corresponding bromoalkyl benzophenone derivatives with hydrazine and 2-hydroxyethyl hydrazine [Rec. Trav. Chim. 84, 633 (1965)]. Some further 3,4-dihydro-5H-2,3-benzodiazepine derivatives unsubstituted in position 1 have also been described [Chem. Ber. 95, 2012 (1962); Synthesis 1973, 159 and 1977, 1; Helv. Chim. Acta 59, 2786 (1976)]. The new compounds according to the invention are different from the above-mentioned known derivatives.

According to a feature of the present invention there are provided new 3,4-dihydro-5H-2,3-benzodiazepine derivatives of the general formula (I) and pharmaceutically acceptable acid addition salts thereof,

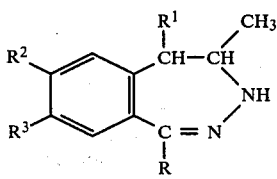

wherein
R represents a phenyl group optionally carrying one or two substituents selected from the group consisting of halogen, hydroxy, $C_{1-4}$ alkoxy and benzyloxy; a furyl or a thienyl group,
$R^1$ stands for a hydrogen atom or a $C_{1-4}$ alkyl group,
$R^2$ and $R^3$ each represent hydrogen atom, $C_{1-4}$ alkoxy, $C_{4-7}$ cycloalkoxy or benzyloxy group.

The term "halogen atom" used in the specification and claims encompasses all the four halogen atoms, such as fluorine, chlorine, bromine and iodine, and it represents preferably chlorine. The term "$C_{1-4}$ alkoxy" refers to straight-chained or branched alkoxy groups containing 1 to 4 carbon atom(s) (e.g. methoxy, ethoxy, n-propoxy, isopropoxy, etc.). The term "$C_{1-4}$ alkyl" covers straight-chained and branched saturated aliphatic hydrocarbyl groups containing 1 to 4 carbon atom(s) (e.g. methyl, ethyl, n-propyl, isopropyl, etc.). Of the $C_{4-7}$ cycloalkoxy groups, e.g. the cyclopropyloxy, cyclobutyloxy, cyclopentyloxy, cyclohexyloxy groups are to be mentioned.

$R^1$ represents preferably a hydrogen atom, a methyl or an ethyl group. $R^2$ and $R^3$ are preferably $C_{1-4}$ alkoxy groups, particularly methoxy groups. The substituents $R^2$ and $R^3$ can be identical or different.

R stands preferably for a phenyl group carrying one or two halogen and/or $C_{1-4}$ alkoxy substituent(s), and it represents particularly a 3-chlorophenyl or 3,4-dimethoxyphenyl group.

Preferred representatives of the compounds having the general formula (I) are those described in the Examples.

A particularly preferred representative of the new compounds of the general formula (I) is the 1-(3-chlorophenyl)-4-methyl-7,8-dimethoxy-3,4-dihydro-5H-2,3-benzodiazepine and the pharmaceutically acceptable acid addition salts thereof.

The pharmaceutically acceptable acid addition salts of the compounds of the general formula (I) can be formed with inorganic or organic acids generally used for this purpose, e.g. with hydrogen chloride, hydrogen bromide, sulfuric, phosphoric, perchloric, maleic, fumaric, succinic, p-toluenesulfonic, lactic acid, etc.

According to a further feature of the present invention there is provided a process for the preparation of new 3,4-dihydro-5H-2,3-benzodiazepine derivatives of the general formula (I) and pharmaceutically acceptable acid addition salts thereof, characterized by reducing a 5H-2,3-benzodiazepine derivative of the general formula (II)

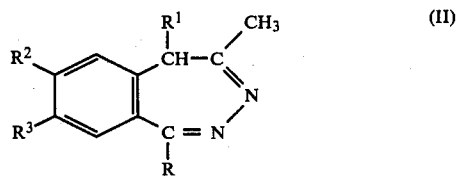

wherein R, $R^1$, $R^2$ and $R^3$ have the above-defined meanings, in a suitable solvent with an inorganic or organic hydride and/or complex metal hydride, and, if desired, converting the compound of the general formula (I) thus-obtained into a pharmaceutically acceptable acid addition salt, or liberating a free base of the general formula (I) from its salt, or converting a salt of a 3,4-dihydro-5H-2,3-benzodiazepine derivative of the general formula (I) into another acid addition salt.

It has been found, surprisingly, that the biological effects of the new compounds of the general formula (I) significantly surpass those of the 5H-2,3-benzodiazepine derivative (tofizopam, 1-(3,4-dimethoxyphenyl)-4-methyl-5-ethyl-7,8-dimethoxy-5H-2,3-benzodiazepine, Hungarian patent specification No. 155,572.).

The selective reduction of the compounds of the general formula (II) can be carried out with known hydrides and complex metal hydrides. For this purpose the following reducing agents are preferably used: sodium hydride, lithium hydride, calcium hydride, diborane, silane, diethyl silane, lithium aluminium hydride, potassium borohydride, sodium borohydride, sodium borohydride-aluminium chloride, sodium dihydro-bis-(2-methoxy-ethoxy)-aluminate, sodium cyanoborohydride, lithium trimethoxy-aluminium hydride, sodium borohydride-triethyloxonium fluoroborate or sodium acyloxy-borohydride.

The reduction is preferably carried out in a solvent or in a mixture of solvents. For this purpose the following solvents are preferably used: water, ethers, alcohols, primary amines, aromatic hydrocarbons, chlorinated aliphatic hydrocarbons, aliphatic carboxylic acids, pyridine.

The reaction medium actually used depends on the reducing agent. It is preferable to carry out the reduction in a solvent or in a mixture of solvents which does not react (or reacts only very slowly) with the hydride or complex metal hydride applied.

The reaction temperature varies between about 10° C. and 100° C. The reducing agent is preferably used in an excess of 50 to 300%.

The compounds of the general formula (I) thus-obtained can be converted, if desired, into acid addition salts in a known way. The salt formation can also serve for the purification of the compounds of the general formula (I). In this case the salts of the compounds of the general formula (I) formed preferably with thiocyanic, p-toluenesulfonic or perchloric acid are prepared, and the bases of the general formula (I) can be liberated from these salts with a suitable strong base (e.g. alkali hydroxide, alcali cabonate, etc.), and, if desired, converted again into other acid addition salts.

The starting substances of the general formula (II) are known compounds or can be prepared by methods described in the literature [Hungarian patent specification No. 155,572; published Hungarian patent application No. T/21372; Chem. Ber. 107, 3883 (1974)].

Based on the results of the pharmacological studies the new 3,4-dihydro-5H-2,3-benzodiazepine derivatives of the invention possess significant central nervous effects (e.g. spontaneous motor activity decreasing, analgetic, narcosis potentiating effect, etc.).

The pharmaceutic effects of the new compounds of the invention are summarized in the following Tables. The effects of a few representatives of the compounds of the general formula (I) on the general behaviour of the test animals—as well as the data concerning the narcosis potentiating effect—are given in Table 1.

TABLE 1

| Compound /No. of Example/ | General behaviour /Dosage:100 mg/kg i.p., mice/ | Narcosis potentiating effect | | |
|---|---|---|---|---|
| | | mg/kg p.o. | increase /%/ | relative activity |
| tofizopam | decrease of SMA | 25 | 81 | 1.0 |
| | | 50 | 114 | 1.0 |
| 3. | strong decrease of SMA | 25 | 294 | 3.63 |
| | | 50 | 825 | 7.24 |
| 9. | strong decrease of SMA | 50 | 327 | 2.87 |
| 10. | — | 50 | 283 | 2.48 |
| 11. | decrease of SMA | 50 | 260 | 2.28 |
| 12. | strong decrease of SMA | 50 | 382 | 3.35 |
| 15. | decrease of SMA | 50 | 131 | 1.15 |
| 16. | no symptom | 50 | 315 | 2.76 |
| 17. | no symptom | 50 | 600 | 5.26 |
| 18. | no symptom | 50 | 440 | 3.86 |
| 19. | decrease of SMA | 50 | 122 | 1.07 |
| 20. | decrease of SMA | 50 | 300 | 2.63 |
| 21. | decrease of SMA | 50 | 280 | 2.46 | tofizopam: 1-(3,4-dimethoxyphenyl)-4-methyl-5-ethyl-7,8-dimethoxy-5H—2,3-benzodiazepine
SMA = spontaneous motor activity Note: the narcosis potentiating effect was studied on mice. The compounds were administered in oral doses of 25 and 50 mg/kg. 30 minutes later 50 mg/kg of sodium hexobarbital were injected intravenously into the animals. The percentage prolongation of the narcosis period, compared to the value observed in the control group treated with sodium hexobarbital alone, was calculated. Tofizopam was applied as reference substance.

The data obtained at the "fighting mice" test are summarized in Table 2.

TABLE 2

| Compound /No. of Example/ | "Fighting mice" test | | |
|---|---|---|---|
| | Dosage /mg/kg, p.o./ | Inhibition /%/ | Relative activity |
| tofizopam | 25 | 37 | 1.0 |
| | 50 | 59 | 1.0 |
| | 100 | 90 | 1.0 |
| 3. | 25 | 64 | 1.73 |
| | 50 | 100 | 1.70 |
| 12. | 50 | 73 | 1.24 |
| 16. | 100 | 90 | 1.00 |
| 20. | 100 | 90 | 1.00 |

Note: the tranquillizer effect was studied according to the method of Tedeschi et al. ["fighting mice" test, J. Pharm. Exp. Ther. 25, 28 (1959)].

Some of the compounds of the general formula (I), (e.g. the derivatives prepared according to the Examples 1, 13, 14, and 15), possess, in addition to their tranquillizer properties, an analgetic effect of the same order of magnitude as that of the Amidazophen (Fed. Proc. 18, 412 (1959)).

The data of the above Tables clearly demonstrate that the new compounds according to the invention possess advantageous biological properties exceeding those of tofizopam.

According to a further feature of the present invention there are provided new pharmaceutical compositions containing as active agent at least one compound of the general formula (I) or a pharmaceutically acceptable acid addition salt thereof, together with a conventional inert, non-toxic, solid or liquid carrier and/or additive.

The pharmaceutical compositions can be formulated in solid (such as tablets, coated tablets, capsules, etc.) or in liquid forms (such as solutions, suspensions, emulsions, etc.). The carriers may be such as generally used in pharmacy (e.g. starch, magnesium stearate, magnesium carbonate, talc, stearin, gelatin, lactose, cellulose, calcium carbonate, polyvinyl pyrrolidone, water, polyalkylene glycole, etc.). The compositions may also contain suitable additives (e.g. suspending, emulsifying, stabilizing agents, buffers, etc.) and therapeutically valuable further agents.

The compositions can be presented in the form of orally, parenterally or rectally administerable preparations.

The pharmaceutical compositions can be prepared by methods generally applied in the pharmaceutical industry.

The invention is elucidated in detail by the aid of the following non-limiting Examples. The compounds were identified by elementary analysis (maximal deviation from the values calculated: ±0.3%) and by IR, $^1$H-NMR and/or mass spectroscopy. The IR and $^1$H-NMR spectra prove that when a salt is formed from the compounds of the general formula (I), the proton is bound by the N-3 atom.

EXAMPLE 1

Preparation of 1-(3,4-dimethoxyphenyl)-4-methyl-5-ethyl-7,8-dimethoxy-3,4-dihydro-5H-2,3-benzodiazepine hydrochloride A mixture of 100 g (0.026 moles) of 1-(3,4-dimethoxyphenyl)-4-methyl-5-ethyl-7,8-dimethoxy-5H-2,3-benzodiazepine, 30 g (0.8 moles) of sodium borohydride and 150 ml of pyridine is stirred on a water bath in a 5

1 round-bottomed flask. A solution containing only a least amount of solid sodium bromide is obtained. The heating is then ceased and 150 ml of water is dropped to the solution. A strong gas evolution (hydrogen) occurs, and the inner temperature decreases to 60° C. Thereafter 1400 ml of water are added to the reaction mixture, and 600 ml of an aqueous hydrochloric acid solution containing 260 ml of concentrated hydrochloric acid are dropwise added to it within an hour, at a temperature between 8° and 15° C. The crystallizing reaction mixture is stirred further for 2 hours, then filtered, washed four times with 50 ml of ice-cold water each and dried. 111.34 g (99.4%) of the desired compound (a pale yellowish crude product decomposing at 218° to 220° C.) are obtained. When recrystallized from isopropanol or anhydrous ethanol the decomposition point rises to 222° to 224° C. The yield of the recrystallization can be increased by adding ethyl acetate, acetone or diethyl ether to the mixture.

When recrystallized from water, the product obtained contains 3 moles of crystal water and decomposes similarly at 222° to 224° C.

The same product can be obtained with a similar yield when using as starting substance—instead of the 5H-2,3-benzodiazepine base—an appropriate amount of the hydrochloride thereof.

EXAMPLE 2

Preparation of
1-(3,4-dimethoxyphenyl)-4-methyl-5-ethyl-7,8-dimethoxy-3,4-dihydro-5H-2,3-benzodiazepine To a suspension of 42.1 g (0.1 mole) of 1-(3,4-dimethoxyphenyl)-4-methyl-5-ethyl-7,8-dimethoxy-3,4-dihydro-5H-2,3-benzodiazepine hydrochloride in 400 ml of water (or to a solution of the said compound in hot water), 8 g of potassium carbonate are added in small parts. The desired compound separates in form of crystals containing 1 mole of crystal water. The product is filtered off, washed chloride-free five times with 15 ml of water each and dried. 34 g (85%) of the desired compound are obtained. The white crude product shrinks from 75° C., between 105° and 115° C. it forms a bubbly coagulate.

The recrystallization of the compound from alcohols (e.g. methanol, anhydrous ethanol, isopropanol) is preferably carried out after removing the crystal water thereof. In this way a pure compound ($C_{22}H_{28}N_2O_4$) melting at 120° to 122° C. is obtained.

Instead of using potassium carbonate, the base can also be liberated with sodium carbonate, sodium bicarbonate or ammonium hydroxide.

The yield given above can be increased by shaking the solution of the compound of the Example 1 in chloroform or in methylene chloride with an aqueous solution of any of the inorganic bases listed above, or by carrying out the liberation in methanol, ethanol or isopropanol with organic bases, e.g. triethyl amine or pyridine.

EXAMPLE 3

Preparation of
1-(3-chlorophenyl)-4-methyl-7,8-dimethoxy-3,4-dihydro-5H-2,3-benzodiazepine Into a 750 ml round-bottomed flask equipped with a stirrer, a dropping funnel and a reflux condenser 9.87 g (0.03 moles) of 1-(3-chlorophenyl)-4-methyl-7,8-dimethoxy-5H-2,3-benzodiazepine, 25 ml of pyridine and 4.5 g (0.12 moles) of sodium borohydride are introduced, and the reaction mixture is stirred on a 95° C. to 100° C. water bath for 4 hours. A yellowish solution containing a certain amount of unreacted sodium borohydride is obtained. 25 ml of water are dropped to it within 30 minutes under cooling. Then a mixture of 56 ml (0.7 moles) of concentrated hydrochloric acid and 110 ml of water are dropped to the reaction mixture in one hour under ice-cooling and stirring.

When 60 ml of the above mixture have already been added, a precipitate begins to separate from the solution. Finally it turns into yellowish clumps. Cooling is then ceased and the mixture is stirred further for 30 minutes at room temperature. A great part of the clumpy, soft precipitation dissolves. The crude final product is obtained by dropping 60 ml of an aqueous sodium hydroxide solution containing 20 g (0.5 moles) of sodium hydroxide to the mixture in 15 minutes. The separated product is soft, but it solidifies in course of further stirring. The clumps are squashed, filtered off, washed four times with 20 ml of water each, finally dried at 50° to 60° C. Yield: 9.6 g (96.5%). M.p.: 116° to 120° C.

The crude product is obtained with a similarly high yield when subjecting the reaction mixture—after the alkalization thereof—to extraction (e.g. from chloroform).

The crude product is recrystallized from 30 ml of isopropanol. Yield: 8.5 g (85.5%). The white product melts at 121° to 123° C. Molecular formula: $C_{18}H_{19}ClN_2O_2$.

The hydrochloride ($C_{18}H_{19}ClN_2O_2 \cdot HCl$) of the product melts at 216° to 218° C. (from isopropanol or from the mixture of isopropanol and ethylacetate).

Instead of pyridine, other solvents [e.g. methanol, primary amines, acetic acid (Example 6) or the mixtures thereof formed with methylene chloride or ethylene chloride] can also be used as reaction medium.

EXAMPLE 4

Preparation of
1-(3,4-dimethoxyphenyl)-4-methyl-5-ethyl-7,8-dimethoxy-3,4-dihydro-5H-2,3-benzodiazepine A 70% benzene solution of 90 ml (0.6 moles) of $NaAlH_2(OCH_2CH_2OCH_3)_2$ is diluted with 90 ml of benzene. The solution thus-obtained is added, within 20 minutes, under stirring, to a solution of 114.6 g (0.3 moles) of 1-(3,4-dimethoxyphenyl)-4-methyl-5-ethyl-7,8-dimethoxy-5H-2,3-benzodiazepine in 1500 ml of benzene. The inner temperature rises to 33° to 35° C. Then the reaction mixture is heated to boiling, within 30 minutes (the gas evolution ceases), recooled to 20° C., and 450 ml of a 20% sodium hydroxide solution (or, in case of compounds containing phenolic hydroxy groups, an aqueous sodium carbonate solution) are dropped to it. A two-phase light yellowish mixture is obtained.

The benzene phase is separated, shaken four times with 350 ml of water each, dried over anhydrous magnesium sulfate and evaporated. The residue (120 g) thus-obtained is recrystallized from 100 ml of methanol to yield 106.5 g (91.5%) of the desired compound ($C_{22}H_{28}N_2O_4$). M.p.: 118° to 120° C.

When recrystallized from isopropanol the melting point rises to 121° to 123° C.

EXAMPLE 5

Preparation of
1-(3,4-dimethoxyphenyl)-4-methyl-5-ethyl-7,8-dimethoxy-3,4-dihydro-5H-2,3-benzodiazepine hydrobromide To a solution of 3.84 g (0.01 mole) of the compound prepared according to the Example 4 in 25 ml of isopropanol 1.1 ml of a 48% aqueous hydrogen bromide solution (or isopropanol containing 0.01 mole of hydrogen bromide, saturated with gaseous hydrogen bromide) are added. The reaction mixture is cooled and washed with a few isopropanol. 4.15 g (90%) of the desired compound ($C_{22}H_{28}N_2O_4 \cdot HBr$) are obtained. The product decomposes at 210° to 213° C. After recrystallization from isopropanol it decomposes at 214° to 215° C.

The salt formation can also be carried out from the crude base by using ethyl acetate, a mixture of isopropanol and acetone or isopropanol and diethyl ether as medium instead of isopropanol.

EXAMPLE 6

Preparation of
1-(3,4-dimethoxyphenyl)-4-methyl-5-ethyl-7,8-dimethoxy-3,4-dihydro-5H-2,3-benzodiazepine To a solution of 3.82 g (0.01 mole) of 1-(3,4-dimethoxyphenyl)-4-methyl-5-ethyl-7,8-dimethoxy-5H-2,3-benzodiazepine in 38 ml of glacial acetic acid a solution of 3 g of sodium borohydride in 10 ml of water is dropped within 2 hours at 3° to 8° C., under stirring. Then the reaction mixture is stirred further for 5 hours at 20° to 25° C. and evaporated in vacuo. The residue (18 g) is dissolved in 30 ml of water, and 10 ml of a 40% sodium hydroxide solution are added. The product separated in soft form crystallizes after cooling. Yield: 3.1 g. The product shrinks from 75° C. The pure compound can be obtained by proceeding as described in Example 2. Yield: 2.29 g. M.p.: 120° to 122° C. Molecular formula: $C_{22}H_{28}N_2O_4$.

EXAMPLE 7

Purification of the compounds of the general formula (I) through the well crystallizable salts thereof The compounds of the general formula (I) having a low melting point or being contaminated with starting substances can be purified not only by column chromatography but also through their salts formed with thiocyanic, p-toluenesulfonic or perchloric acid. The rhodanate of the compounds according to Example 2 ($C_{22}H_{28}N_2O_4 \cdot HSCN$) decomposes at 214° to 216° C. (it is prepared by reacting the pure or the crude compound according to Example 2 with ammonium rhodanate and then recrystallizing from water or from an aqueous solution containing 90% of isopropanol). The p-toluenesulfonate ($C_{22}H_{28}N_2O_4 \cdot C_7H_8O_3S$) melts at 173° to 175° C. (it is prepared from the compound of Example 2 in acetone). The perchlorate ($C_{22}H_{28}N_2O_4 \cdot HClO_4$) decomposes at 215° to 217° C. (it is prepared from the compound according to Example 2 in isopropanol and recrystallized from a 90% isopropanol solution).

From these salts the bases ca be liberated e.g. by the method described in Example 2.

EXAMPLES 8 to 21

The compounds of the general formula (I) listed in Table 3 can be prepared by the methods described in Examples 1 to 7.

Key to the signs used in Table 3:
d. = decomposition point
The letters in brackets = solvents used for the recrystallization:
 [a] = isopropanol
 [b] = 50% ethanol
 [c] = ethanol or anhydrous ethanol
 [d] = a mixture of isopropanol and ethyl acetate, acetone or diethyl ether
 [e] = 90% isopropanol

TABLE 3

| No. of Example | R | $R^1$ | $R^2$ | $R^3$ | Method /No. of Example/ | Molecular formula of the base or the salt | M.p. /°C./ /Recryst./ |
|---|---|---|---|---|---|---|---|
| 8. | 3-hydroxy-4-isopropoxy-phenyl | Et | MeO | iPrO | 3. | $C_{26}H_{36}N_2O_4$ | 124–126 [a] |
| 9. | 3,4-dimethoxyphenyl | Et | cyclopentyloxy | MeO | 3. | $C_{26}H_{34}N_2O_4$ | 102–104 [b] |
| 10. | 2-furyl | H | MeO | MeO | 3. | $C_{16}H_{18}N_2O_3$ | 148–150 [c] |
| 11. | 2-thienyl | H | MeO | MeO | 3. | $C_{16}H_{18}N_2O_2S$ | 151–153 [c] |
| 12. | 3-fluorophenyl | H | MeO | MeO | 3. | $C_{18}H_{19}FN_2O_2$ | 118–120 [c] |
| 13. | 3-methoxy-4-n-butoxyphenyl | Et | MeO | nBuO | 4., 5. | $C_{28}H_{40}N_2O_4 \cdot HCl$ | 147–149 [d] |
| 14. | 3-methoxy-4-benzyloxy-phenyl | Et | MeO | PhCH$_2$O | 4., 5. | $C_{34}H_{36}N_2O_4 \cdot HCl$ | 208–210 d. [c] |
| 15. | 3,4-dimethoxyphenyl | Me | MeO | MeO | 1. | $C_{21}H_{26}N_2O_4 \cdot HCl$ | 232–233 d. [e] |
| 16. | 2-chlorophenyl | Et | MeO | MeO | 3. | $C_{20}H_{23}ClN_2O_2$ | 177–179 [c] |
| 17. | 3,4-dimethoxyphenyl | nBu | MeO | MeO | 3. | $C_{24}H_{32}N_2O_4$ | 88–90 [b] |
| 18. | 2-chlorophenyl | H | MeO | MeO | 3. | $C_{18}H_{19}ClN_2O_2$ | 126–128 [c] |
| 19. | 3-chlorophenyl | Me | MeO | MeO | 3. | $C_{19}H_{21}ClN_2O_2$ | 124–126 [c] |
| 20. | 3,5-dichlorophenyl | H | MeO | MeO | 3. | $C_{18}H_{18}Cl_2N_2O_2$ | 140–142 [c] |
| 21. | 3-chlorophenyl | H | EtO | EtO | 3. | $C_{20}H_{23}ClN_2O_2$ | 116–118 [b] |

EXAMPLE 22

Preparation of pharmaceutical compositions

Tablets containing 20 mg of active agent [e.g. 1-(3-chlorophenyl)-4-methyl-7,8-dimethoxy-3,4-dihydro- 5H-2,3-benzodiazepine] are prepared in a manner known per se. The composition of one tablet is as follows:

| Active ingredient | 20.0 mg |
|---|---|
| Magnesium stearate | 1.0 mg |
| Stearin | 1.0 mg |
| Talc | 2.0 mg |
| Gelatin | 3.5 mg |
| Maize starch | 20.5 mg |
| Lactose | 122.0 mg |
| Microcrystalline cellulose | 10.0 mg |
| | 180.0 mg |

EXAMPLE 23

Preparation of pharmaceutical compositions

Dragées containing 20.0 mg of active ingredient [e.g. 1-(3-chlorophenyl)-4-methyl-7,8-dimethoxy-3,4-dihydro-5H-2,3-benzodiazepine] are prepared in a manner known per se. The composition of a dragée kernel is as follows:

| Active ingredient | 20.0 mg |
|---|---|
| Maize starch | 16.0 mg |
| Magnesium stearate | 1.0 mg |
| Lactose | 38.0 mg |
| Polyvinyl pyrrolidone | 5.0 mg |
| | 80.0 mg |

The dragée kernels are coated by a layer containing sugar and talc. The weight of a finished dragée is 120 mg.

The other compounds of the general formula (I) can also serve as active agents of pharmaceutical compositions.

What we claim is:

1. 3,4-Dihydro-5H-2,3-benzodiazepine derivatives of the formula (I) and pharmaceutically acceptable acid addition salts thereof, $$\text{(I)}$$

wherein
R represents a phenyl group optionally carrying one or two substituents selected from the group consisting of halogen, hydroxy, $C_{1-4}$ alkoxy and benzyloxy; a furyl or a thienyl group,
$R^1$ stands for a hydrogen atom or a $C_{1-4}$ alkyl group,
$R^2$ and $R^3$ each represent hydrogen atom, $C_{1-4}$ alkoxy, $C_{4-7}$ cycloalkoxy or benzyloxy group.

2. Compounds as claimed in claim 1, wherein R stands for a phenyl group carrying one or two $C_{1-4}$ alkoxy and/or halogen substituent(s).

3. Compounds as claimed in claim 2, wherein R represents a 3-chlorophenyl or 3,4-dimethoxyphenyl group.

4. Compounds as claimed in any one of claims 1 to 3, wherein $R^2$ and $R^3$ represent methoxy groups.

5. 1-(3-Chlorophenyl)-4-methyl-7,8-dimethoxy-3,4-dihydro-5H-2,3-benzodiazepine and pharmaceutically acceptable acid addition salts thereof.

6. A process for the preparation of new 3,4-dihydro-5H-2,3-benzodiazepine derivatives of the formula (I) and pharmaceutically acceptable acid addition salts thereof, $$\text{(I)}$$

wherein
R represents a phenyl group optionally carrying one or two substituents selected from the group consisting of halogen, hydroxy, $C_{1-4}$ alkoxy and benzyloxy; a furyl or a thienyl group,
$R^1$ stands for a hydrogen atom or a $C_{1-4}$ alkyl group,
$R^2$ and $R^3$ each represent hydrogen atom, $C_{1-4}$ alkoxy, $C_{4-7}$ cycloalkoxy or benzyloxy group,
characterized by reducing a 5H-2,3-benzodiazepine derivative of the formula (II)

$$\text{(II)}$$

wherein
R, $R^1$, $R^2$ and $R^3$ have the above-defined meanings, in a suitable solvent with an inorganic or organic hydride and/or complex metal hydride, and, if desired, converting the compound of the formula (I) thus-obtained into a pharmaceutically acceptable acid addition salt, or liberating a free base of the formula (I) from its salt, or converting a salt of a 3,4-dihydro-5H-2,3-benzodiazepine derivative of the formula (I) into another acid addition salt.

7. A process as claimed in claim 6, characterized by using as reducing agent sodium hydride, lithium hydride, calcium hydride, diborane, silane, diethyl silane, lithium aluminium hydride, potassium borohydride, sodium borohydride-aluminium chloride, sodium dihydro-bis-(2-methoxy-ethoxy)-aluminate, sodium cyanoborohydride, lithium trimethoxy-aluminium hydride, sodium borohydride-triethyloxonium fluoroborate or sodium acyloxy-borohydride.

8. A process as claimed in claim 6 or 7, characterized by carrying out the reaction in a solvent or in a mixture of solvents which does not react, or only very slowly, with the hydride or complex metal hydride applied.

9. A pharmaceutical composition containing as an active ingredient an effective amount of at least one compound of the formula (I) as described in claim 1 or a pharmaceutically acceptable acid addition salt thereof, together with a conventional inert, non-toxic, solid or liquid carrier and/or additive.

* * * * *